United States Patent [19]
Judet et al.

[11] Patent Number: 5,591,168
[45] Date of Patent: Jan. 7, 1997

[54] DEVICE FOR STABILIZING FRACTURES OF THE UPPER END OF THE FEMUR

[75] Inventors: Thierry Judet, Ville d'Avray; Gérard Saillant, Celle Saint Cloud, both of France

[73] Assignee: Tornier S.A., Saint-Ismier, France

[21] Appl. No.: 643,835

[22] Filed: May 7, 1996

Related U.S. Application Data

[63] Continuation of Ser. No. 328,665, Oct. 25, 1994, abandoned.

[30] Foreign Application Priority Data

Oct. 25, 1993 [FR] France .................................. 93 12899

[51] Int. Cl.⁶ .......................... A61B 17/56; A61B 17/58
[52] U.S. Cl. .................... 606/65; 606/72; 606/69
[58] Field of Search ............................ 606/65, 66, 67, 606/68, 69, 70, 71

[56] References Cited

U.S. PATENT DOCUMENTS

| | | |
|---|---|---|
| 2,772,676 | 12/1956 | Pohl . |
| 3,489,143 | 1/1970 | Halloran ........................ 606/67 |
| 3,554,193 | 1/1971 | Konstantinou ................. 606/65 |
| 3,824,995 | 7/1974 | Getscher et al. .............. 606/69 |
| 5,007,910 | 4/1991 | Anapliotis et al. ............ 606/65 |

FOREIGN PATENT DOCUMENTS

| | | |
|---|---|---|
| 0382256 | 8/1990 | European Pat. Off. .............. 606/67 |
| 2289154 | 10/1974 | France . |
| 303830 | 6/1916 | Germany . |
| 0515828 | 5/1991 | Switzerland . |
| 8102388 | 9/1981 | WIPO . |

*Primary Examiner*—Michael Powell Buiz
*Assistant Examiner*—Mark S. Leonardo
*Attorney, Agent, or Firm*—Dowell & Dowell

[57] ABSTRACT

A device for stabilizing fractures of the upper end of the femur, comprising a plate which includes in its upper part two parallel, cylindrical barrels offset by a first angle with respect to a vertical plane passing through the middle of the plate and a second angle with respect to a horizontal axis passing through the middle of the plate.

6 Claims, 3 Drawing Sheets

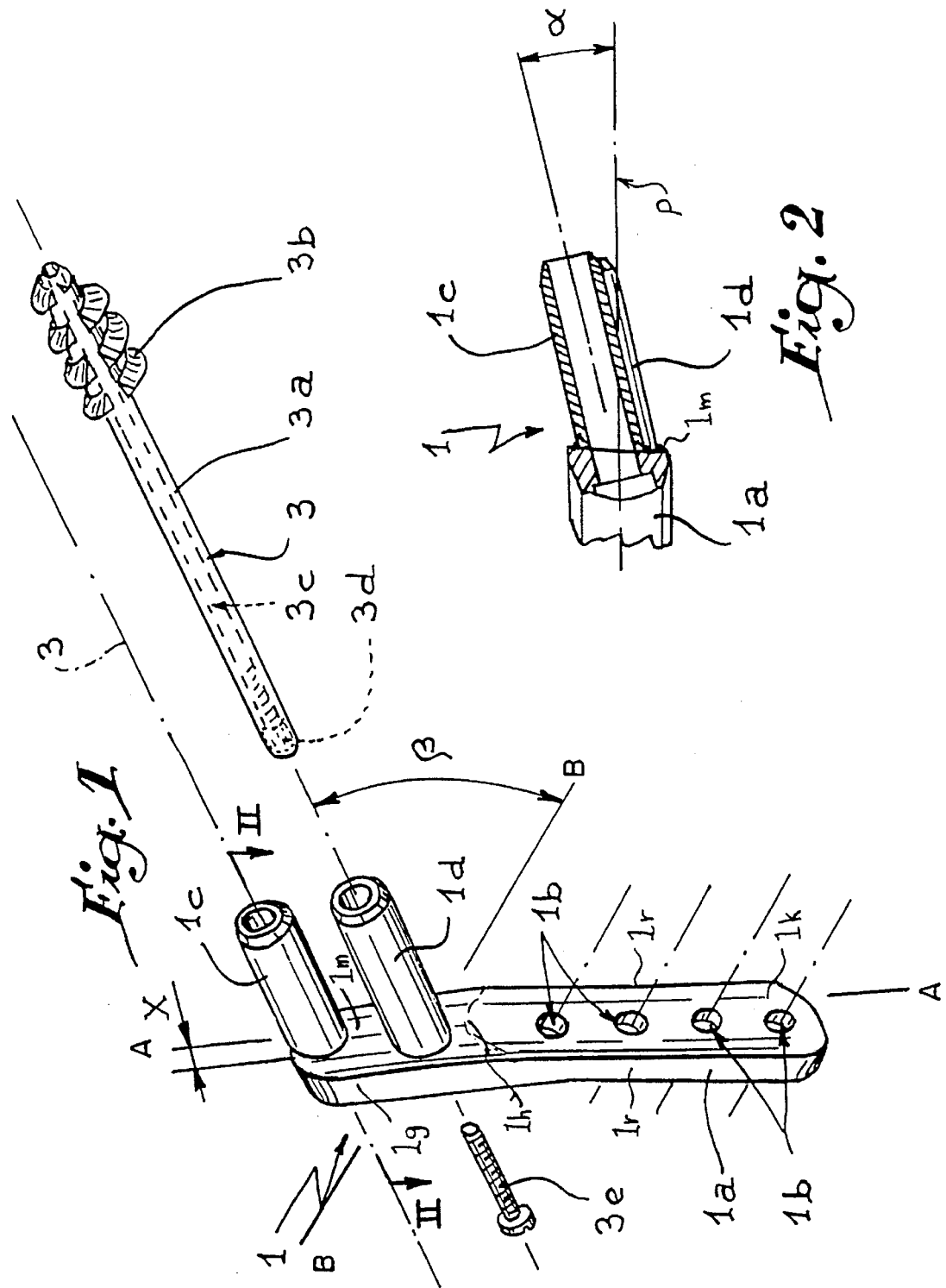

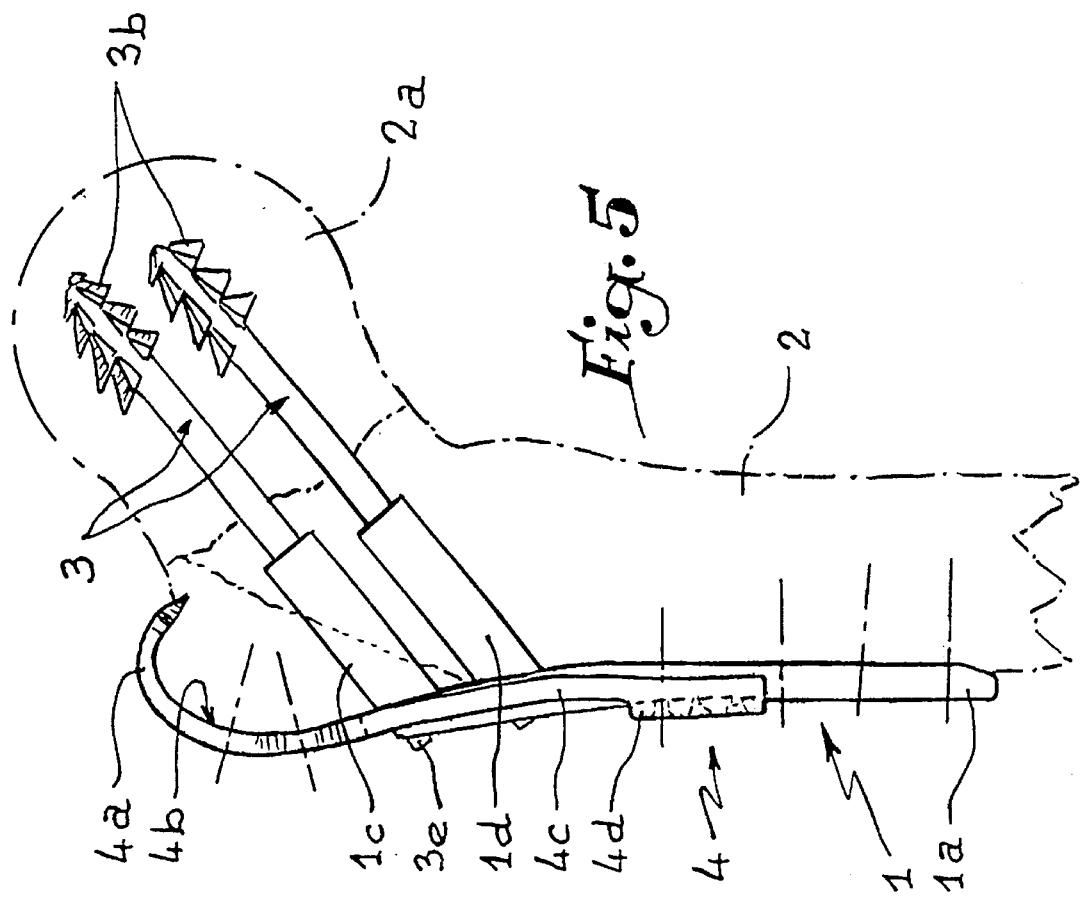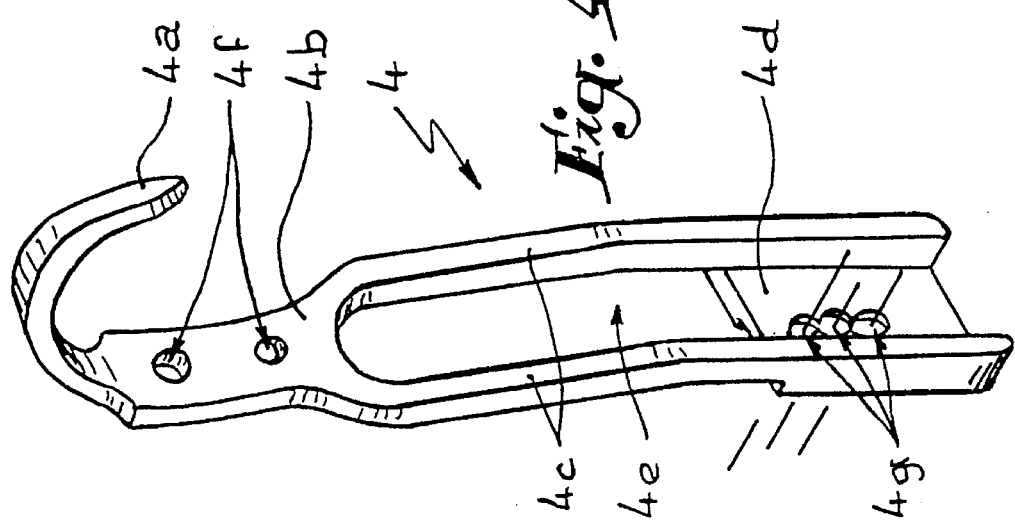

DEVICE FOR STABILIZING FRACTURES OF THE UPPER END OF THE FEMUR

This application is a continuation of Ser. No. 08/328,665, filed Oct. 25, 1994, now abandoned.

BACKGROUND OF THE INVENTION

1. Field of the Invention

The present invention relates to a device for stabilizing fracture of the upper end of the femur.

2. History of the Related Art

Devices of this type are known, which generally comprise a plate screwed in the upper part of the femur. This plate comprises a smooth, cylindrical barrel which is introduced inside a bore previously made in the internal part of the femur. The barrel allows a traction screw to be positioned, which is placed under tension in order to draw the cephalic sphere nearer the body of the femur.

This device is too fragile and its cephalic hold is insufficient, this leading to risks of axial rotation of the cephalic sphere or femoral head, in addition, these devices expose patients to risks of dislocations, infections of or cotyloiditis.

it is a particular object of the present invention to overcome these drawbacks.

The purpose of the device according to the present invention is to improve the anchoring between the cephalic sphere or femoral head and the femur with a view to preventing any rotation of the sphere with respect to the body of femur. Moreover, the structure of this device enables patients to resume the upright position and to walk soon after an operation.

SUMMARY OF THE INVENTION

The device according to the present invention comprises a plate screwed in the femur and comprising in its upper part two parallel, cylindrical barrels which are offset, on the one hand, by a first angle $\alpha$ with respect to the vertical plane passing through the middle of said plate and, on the other hand, by a second angle $\beta$ with respect to the horizontal axis packing through the middle of the plate.

In addition, the barrels are offset laterally with respect to each other by a distance X in order to correspond perfectly to the morphology of the femur.

BRIEF DESCRIPTION OF THE DRAWINGS

The invention will be more readily understood on reading the following description with reference to the accompanying drawings, in which:

FIG. 1 is a view in perspective illustrating the plate constituting the device according to the present invention.

FIG. 2 is a section along line II—II (FIG. 1) showing the offset of the barrels towards the right of left outside edges of the plate of FIG. 1.

FIG. 4 and 5 are views illustrating a trochanter hook which improves the fixation of the plate in the femur.

DESCRIPTION OF PREFERRED EMBODIMENT

Figure 3:
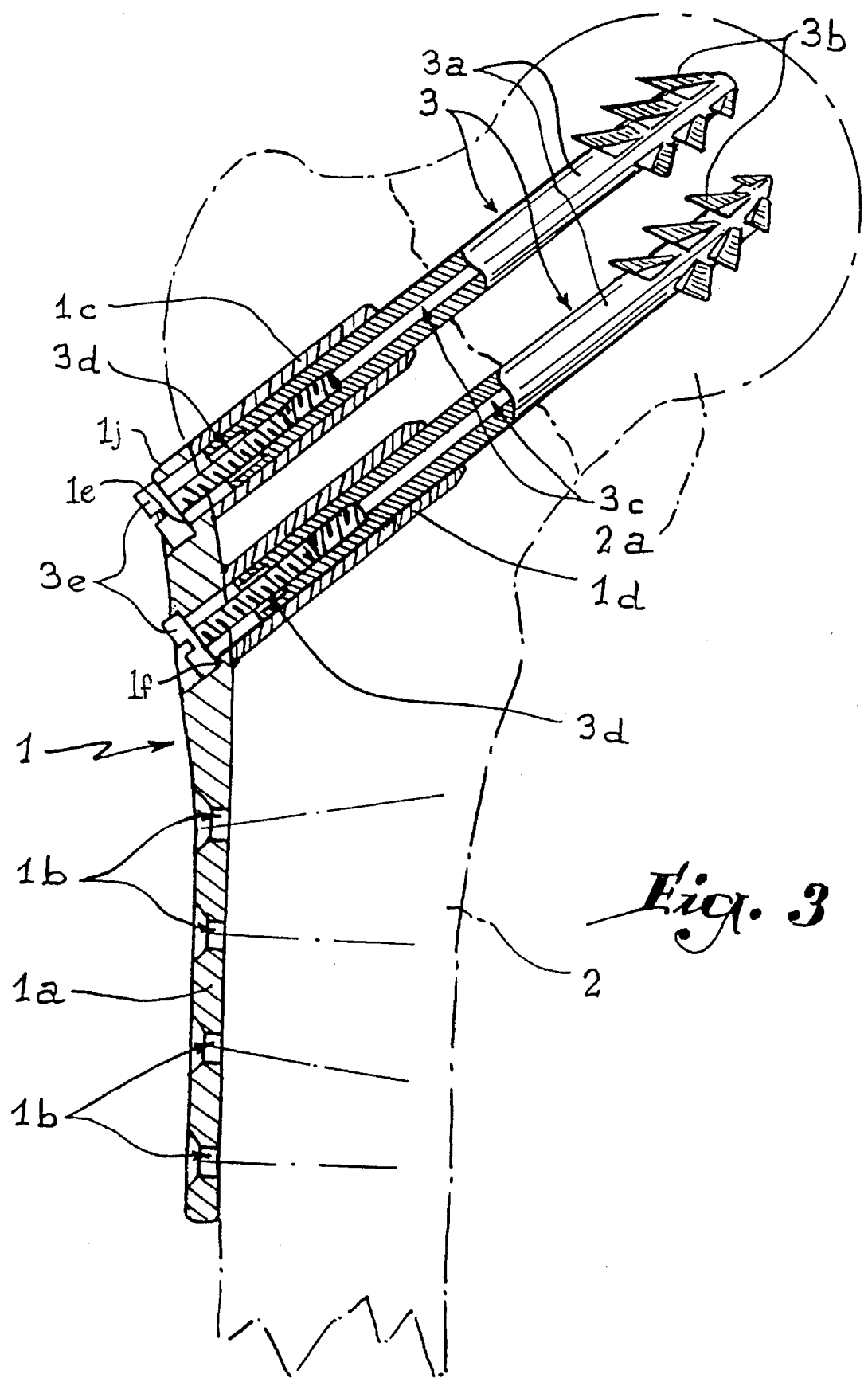
FIG. 3 is a longitudinal section showing the positioning of the plate with respect to repairing a fracture of the femoral head.

Referring now to the drawings, FIGS. 1 to 3 show a device 1 for setting fractures of the upper end of a femur 2. This device is provided to replace the cephalic sphere or femoral head 2a on the body of the femur 2.

Device 1 comprises a plate 1a whose profile is adapted to the outer curvature of the femur 2. The lower part 1k of plate 1a is provided with a plurality of holes 1b which allow fixation thereof on the femur 2.

The upper part 1g of the plate 1a is arcuate in form with respect to its lower part, as shown in FIG. 3 so as perfectly to match the outer curvature of the femur 2 and more particularly below the greater trochanter.

The upwardly directed front face 1m of the plate 1a is fixedly secured fast with two cylindrical barrels 1c and 1d whose inner bore is smooth and sliding. Each barrel 1c, 1d is disposed so that its inner bore opens out respectively in a shouldered bore 1e, 1f made in the upper part of the plate 1a. The free end of each of the barrels 1c and 1d is bevelled, and rounded in order to facilitate positioning thereof inside holes previously made in the femur 2, as will be more readily explained hereinafter, Barrels 1c and 1d are parallel to each other and are of different lengths. In fact, the length of barrel 1d is slightly greater than that of barrel 1c.

Barrels 1c and 1d are offset towards the outside of the plate 1a horizontally by a first angle $\alpha$ either to the right or to the left depending on whether the stabilization concerns a right- or left-hand femur. Angle $\alpha$ is equal to about 13° with respect to the vertical plane p passing through the middle of the plate, and generally perpendicular to the front face thereof so as perfectly to correspond to the morphology of the femoral body.

Barrels 1c and 1d are slightly offset with respect to each other by a distance X between the outside edges 1r of the plate to match the torsion of the femoral neck, i.e. the lower barrel 1d is more posterior with respect to the central axis A—A of the plate 1a, while the upper barrel 1c is more exterior with respect to the same axis.

Barrels 1c and 1d are inclined by a second vertical angle $\beta$ with respect to a horizontal axis B—B passing through the middle 1h of the plate 1a. This angle $\beta$ is equal to about 40°.

Positioning of the plate 1a is conventional, i.e. two parallel holes are made in the upper part of the femur 2 for positioning two cephalic screws 3. Each cephalic screw 3 comprises a cylindrical body 3a whose outer diameter is adjusted with respect to that of the bore of the barrels 1c and 1d so as to slide therein. One of the ends of the cylindrical body 3a comprises a thread 3b of self-tapping, conical profile which is anchored inside the cephalic sphere 2a.

The inner part of the cylindrical body 3a is provided with an opening or hole 3c of which the end opposite the thread 3b is provided with a hexagonal bore 3d enabling the screw 3 to be screwed in place inside the cephalic sphere 2a.

In the vicinity of the hexagonal bore 3d, the hole 3c is tapped to receive a screw 3e.

Plate 1a is then fixed against the outer profile of the femur 2 so that the barrels 1c and 1d penetrate therein, cooperating with the cephalic screws 3. A screw 3e is screwed inside each cephalic screw 3 in order to draw on the latter inside the barrels 1c and 1d. Positioning of the device 1 enables the cephalic sphere 2a to be applied against the body of the femur 2 in order to repair a fracture.

FIGS. 4 and 5 show an element 4 which allows stabilization of the mass of the greater trochanter when necessary, in addition to the stabilization of the head and neck of the femur.

Element 4 includes in its upper part a curved profile in the form of a hook 4a, which is single or double depending on the conditions of use, Below hook 4a is provided a bearing face 4b extending in two parallel branches 4c. Branches 4c are joined to each other at lower part by a plate member 4d. Branches 4c define a slot 4e which allows the plate 1a to be placed in position.

The bearing face 4b is pierced with two holes 4f for fixing element 4 in the upper part of the femur 2 and more particularly on the greater trochanter. Plate 4d has a plurality of holes 4g, communicating with respect to one another, to allow a screw to cooperate with the holes 1b made in the lower part of the plate 1a.

Element 4 presents a profile adapted to the outer curvature of the femur, and is mounted astride the plate 1a.

it will be noted that the apex is of time plate 1a is slightly sunk in order not to come into conflict with the muscular ties located at that spot.

Furthermore, it will be noted that several lengths of plates are available in order to correspond to all the anatomical curvatures of the femur 2.

It is also noted that plate 1a is made of a material such as stainless steel or any other bio-compatible material performing a perfect function and safety.

It must, moreover, be understood that the foregoing description has been given only by way of example and that it in no way limits the domain of the invention which would not be exceeded by replacing the details of execution described by any other equivalents.

What is claimed is:

1. A device for stabilizing fractures of the upper end of the femur comprising, a plate having opposite side edges, a lower part having holes therethrough, an upper part and a middle portion between said upper and lower parts, said upper part having a front face, two parallel cylindrical barrels extending from said front face of said upper part which are offset both laterally at a first angle from a first plane extending perpendicularly to said front face and through said plate and generally parallel to said opposite side edges thereof and vertically at a second angle from a second plane extending through said middle portion of said plate generally perpendicularly to said front face and generally perpendicular to said first plane, and said two parallel cylindrical barrels being offset with respect to each other so that one of said barrels is positioned closer to one of said opposite side edges while the other of said barrels is positioned closer to the other of said opposite side edges.

2. The device of claim 1, wherein said front face of said upper part of said plate is arcuate in shape so as to be adapted to the outer curvature of the femur.

3. The device of claim 1, wherein each of said barrels comprise smooth internal bores to allow receipt of anchoring screws.

4. A device for stabilizing fractures of the upper end of the femur comprising, in combination, a plate having opposite side edges, a lower part having holes therethrough, an upper part and a middle portion between said upper and lower parts, said upper part having a front face, two parallel cylindrical barrels extending from said front face of said upper part which are offset both laterally at a first angle from a first plane extending perpendicularly to said front face and through said plate and generally parallel to said opposite side edges thereof and vertically at a second angle from a second plane extending through said middle portion of said plate generally perpendicularly to said front face and generally perpendicular to said first plane, a trochanter element having an upper part in the form of at least one hook, a bearing face extending from said at least one hook, two spaced and parallel branches extending from said bearing face along said opposite side edges of said plate and defining an opening therebetween in which said upper part of said plate is received, said parallel branches having lower ends, and a plate member overlying said plate and joining said lower ends of said parallel branches and having holes therethrough for communicating with said holes in said lower part of said plate whereby fastening elements may be inserted through aligned holes in said plate and said plate member of said trochanter element.

5. The device of claim 4, wherein said bearing face includes holes, and fixation means for extending through said holes in said hearing face.

6. The device of claim 4, wherein said two parallel cylindrical barrels are offset with respect to each other so that one of said barrels is positioned closer to one of said opposite side edges while the other of said barrels is positioned closer to the other of said opposite side edges.

\* \* \* \* \*